United States Patent [19]
Herbreteau et al.

[11] Patent Number: 5,518,049
[45] Date of Patent: May 21, 1996

[54] DEVICE FOR FILLING A RECEPTACLE CLOSED BY A NEEDLE AND PROVIDED WITH CLEANING MEANS

[75] Inventors: Michel Herbreteau, Cherbourg; Robert Marchand, Equeurdreville; Arnaud Delahaye, Sollo Tourlaville, all of France

[73] Assignee: Compagnie Generale des Matieres Nucleaires, Velizy-Villacoublay, France

[21] Appl. No.: 284,125

[22] Filed: Aug. 2, 1994

[30] Foreign Application Priority Data

Aug. 5, 1993 [FR] France .................................. 9309661

[51] Int. Cl.⁶ .................................................. B65B 3/00
[52] U.S. Cl. .................. 141/85; 141/90; 141/91; 141/92; 141/93; 141/130; 141/329
[58] Field of Search .................. 141/85, 70, 89–93, 141/130, 329

[56] References Cited

U.S. PATENT DOCUMENTS

| | | | |
|---|---|---|---|
| 2,519,353 | 8/1950 | Cassady | 141/70 X |
| 2,787,875 | 4/1957 | Johnson | 141/91 X |
| 3,879,795 | 4/1975 | Gfeller | 141/92 X |
| 4,417,607 | 11/1983 | Scholle et al. | 141/92 X |
| 4,498,508 | 2/1985 | Scholle et al. | 141/92 X |
| 4,615,360 | 10/1986 | Jacobs | 141/91 X |
| 4,964,444 | 10/1990 | Hanerus et al. | 141/90 |

FOREIGN PATENT DOCUMENTS

| | | | |
|---|---|---|---|
| 0572988 | 11/1958 | Belgium | 141/85 |
| 63971 | 3/1982 | European Pat. Off. | |
| 78212 | 10/1982 | European Pat. Off. | |
| 472831 | 6/1991 | European Pat. Off. | |
| 511097 | 4/1992 | European Pat. Off. | |
| 522959 | 7/1992 | European Pat. Off. | |
| 0999155 | 10/1951 | France | 141/85 |
| 0926350 | 4/1955 | Germany | 141/92 |
| 2739742 | 3/1979 | Germany | 141/90 |
| 3044424 | 6/1982 | Germany | |

*Primary Examiner*—J. Casimer Jacyna
*Attorney, Agent, or Firm*—Pearne, Gordon, McCoy & Granger

[57] ABSTRACT

Device for filling a receptacle (R) by lowering it onto a needle (5) which pierces it. The portions of the installation adjacent to the bottom of the receptacle (R), which could be polluted by ill-timed projections of liquid from the needle, are washed and dried by nozzles (27, 28, 29) for washing the zones potentially reached by the projections, as well as the needle (5) itself, this washing and drying being followed by drying by suction orifices (38).

10 Claims, 2 Drawing Sheets

5,518,049

DEVICE FOR FILLING A RECEPTACLE CLOSED BY A NEEDLE AND PROVIDED WITH CLEANING MEANS

FIELD OF THE INVENTION

The invention concerns a device for filling a receptacle closed by a needle and provided with cleaning means.

BACKGROUND OF THE INVENTION

The invention is more particularly applicable for use in an installation for analysing dangerous liquids, especially radioactive liquids, where the receptacles containing liquid samples are pneumatically transported in a network of pipes between various stations and in particular analysis stations. However, it is firstly essential to fill the receptacles and this is why one of these stations of the network is allocated to filling. This station mainly comprises at least one filling liquid elevator ended by a needle for piercing the receptacle and a sheath including a bottom pierced in front of the needle. The receptacle to be filled is laid in a cage sliding in the sheath which remains suspended at some distance from the bottom of the sheath for most of the filling operations and which is lowered to the bottom of the sheath so as to provoke the piercing of the bottom of the receptacle by means of the needle.

The drawbacks linked to this conception are linked to pollution of the casing of the receptacle, indeed the bottom of the sheath. The filling liquid elevator may in fact be subject to operating defects expressed by small projections of liquid which splash the receptacle and the bottom of the sheath, or simple oozings which flow along the needle and are deposited on the bottom of the receptacle around the piercing hole. The high speed (15 meters per second) acquired by the receptacles when carried in the pipes then generally provokes a dispersion of small drops in the pipes and brings about pollution likely to extend throughout the entire network owing in particular to movements of the displacement air.

SUMMARY OF THE INVENTION

The invention concerns improving an existing filling installation and seeks to clean the bottom of the receptacle and internal face of the bottom wall of the sheath so as to get rid of the polluting liquids which risk contaminating them.

The invention generally includes a device for filling a closed receptacle including a filling liquid elevator ended by a needle for piercing the bottom of the receptacle, a sheath having a bottom constituted by a wall pierced in front of the needle and mobile to the needle and being connected to a network of pipes for carrying the receptacle by pneumatic means, and a cage situated in the sheath and disposed in such a way so as to suspend the receptacle slightly above the bottom of the sheath, wherein the sheath is equipped with washing liquid suction nozzles towards the bottom of the receptacle suspended in the cage and towards the internal face of the wall of the bottom of the sheath.

The polluting liquid is then made to run down with the washing liquid and flow below the sheath and needle as far as a drain where it can no longer cause damage.

Other means may complete the invention, such as additional nozzles for spraying the washing liquid towards the needle, and means for drying the bottom of the receptacle and internal face of the wall of the bottom of the sheath. Moreover, it is preferable that the nozzles are orientated in such a way as to sprinkle the bottom of the receptacle obliquely and make the washing liquid rebound from the bottom of the receptacle towards the internal face of the bottom of the sheath.

BRIEF DESCRIPTION OF THE DRAWINGS

The invention shall now be described by way of nonrestrictive illustration with the aid of the following figures.

DETAILED DESCRIPTION OF THE PREFERRED EMBODIMENTS

Figure 1:
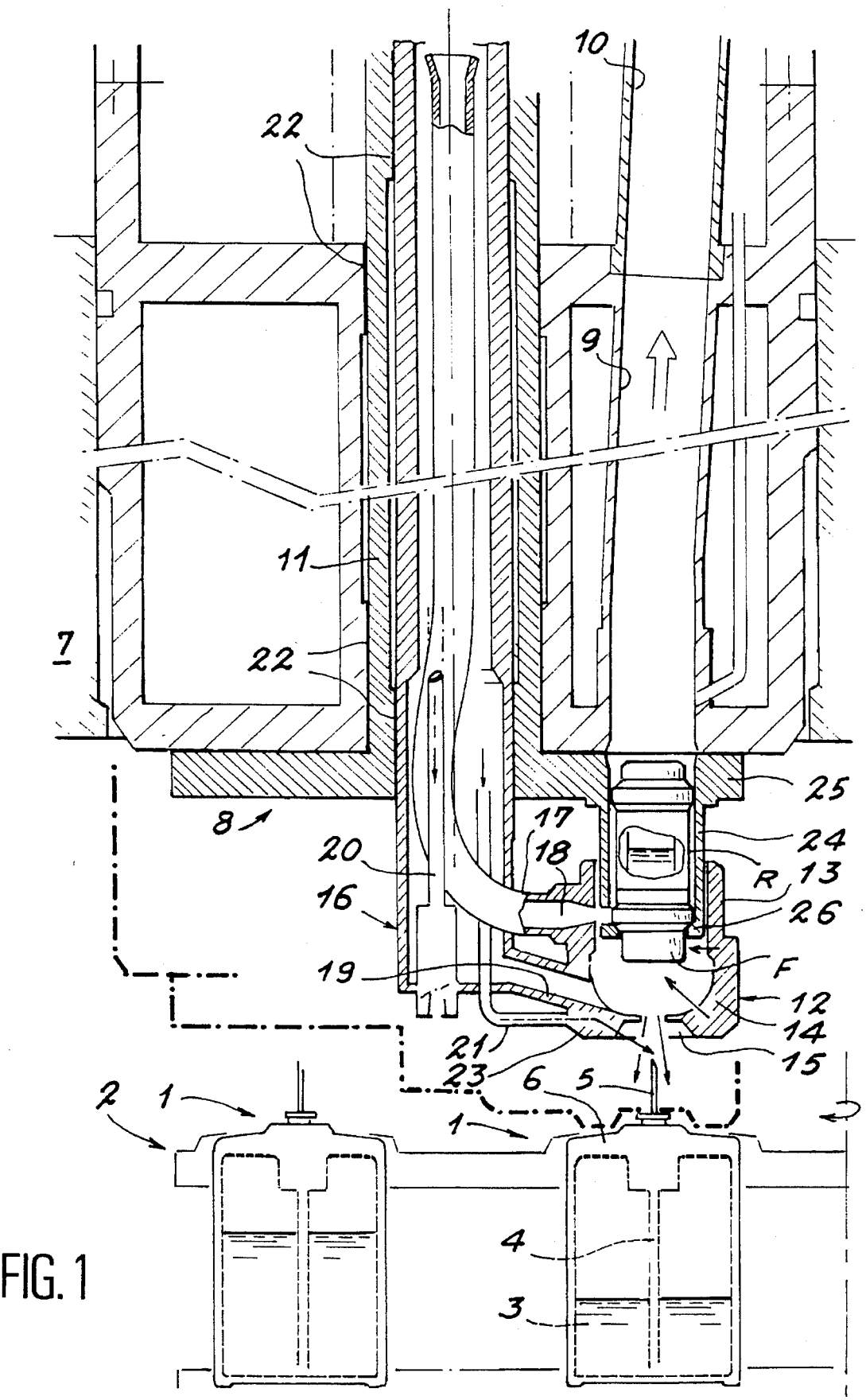
FIG. 1 is a general view of the filling device.

The filling installation in fact includes (FIG. 1) several filling heads 1 disposed along two concentric rings on a tank bottom 2; each of the filling heads 1 is connected to a liquid tank 3 by a bubble elevator 4 ended by a needle 5 secured to a sampling block 6. The tank bottom 2 is in a highly polluted chamber surmounted by a cover or plug 7 which isolates it from the outside but is nevertheless pierced and occupied at the piercing location by a tool carrier 8. The plug 7 rotates with an axis (not shown) which coincides with that of the rings of the filling heads 1.

This tool carrier 8 includes a connecting pipe 9 connected to a network of transport pipes by pneumatic means, one end 10 of the latter being shown and moving vertically until it joins the connecting pipe 9. The tool carrier 8 further includes a median shaft 11 rotating around its axis so as to move a sheath 12, situated firstly under the connecting pipe 9 or above a filling head 1 of one of the rings, above a location of the other ring of the filling heads 1 if required. The median shaft 11 traverses the tool carrier 8 on both sides and extends below the latter.

Figure 2:
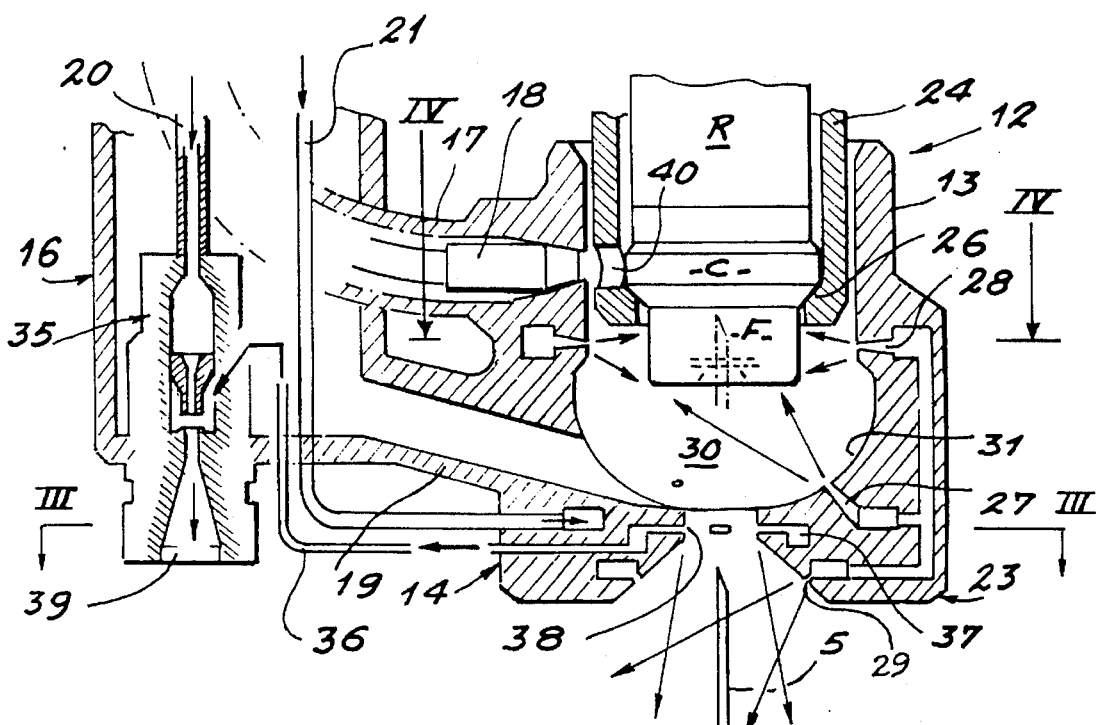
FIG. 2 is a detailed view showing the main portions.

The sheath 12, which is more visible on FIG. 2, includes in particular an upper cylindrical portion 13 joined to a crucible-shaped bottom 14 whose wall has an opening immediately in front of one of the needles 5. This opening is denoted by 15.

The sheath 12 is connected to a hollow piston 16 by an optical fiber pipe 17 which extends into the hollow piston 16 and then traverses its wall so as to end up in the cylindrical portion 13 (the optical fiber is denoted by 18) and by an air connection 19 which opens aside in the bottom 14. The air connection 19 communicates into the inside of the hollow piston 16 which may be filled with air by means (not shown) situated above the tool carrier 8.

With reference to FIG. 1, the hollow piston 16 further contains an air pipe 20 and a water pipe 21 and slides into bearings 22 axially inside the shaft 11 so as to lower the sheath 12 from the position shown to the one indicated by the dot-and-dash lines where a lower small ring 23 raised up under the lower face of the bottom 14 is placed the block 6 around the selected needle 5 which enters the bottom 14 via the piercing 15.

The tool carrier 8 is mobile in the sliding direction of the hollow piston 16 and then drives a cylindrical cage 24 partially contained in the sheath 12 towards the bottom of the latter. The tool carrier 8 bearing the median shaft 11 and the hollow piston 16 are thus independently translationmobile, but the median shaft 11 and the hollow piston 16 are integral in rotation on account of the engagement of the boat 24 in the sheath 12 and the fixing of the cage 24 to a plate 25 moved by the median shaft 11. A receptacle R, known as a "cruchon-cursor" (cursor small jug) by the Applicant, supported and placed in the cage 24 and whose bottom F exceeds the latter by a hole 26 which traverses the internal face of the boat 24, is thus moved and placed above a sampling head 1 selected according to the rotation of the rotating plug 7 and then lowered onto the needle 5 of the sampling head 1 which finally pierces the bottom F. More specifically, the rotation of the rotating plug 7 brings the receptacle R within the range of a sampling head 1 of each of the rings, the choice between these two heads being accomplished by a rotation of the median shaft 11 whose axis is half way between the two rings and on which the receptacle R is moved out of center. An air pressure on the top of the receptacle R may be added to the weight of the receptacle R so as to carry out piercing.

The various mobile elements are driven by electric motors or pneumatic means and transmissions which are not shown as they do not form any original part of the invention and are present on the existing known installation. The pipes are connected to fixed air or water feed pipes (not shown) by means of flexible pipes above the tool carrier 8.

With reference to FIG. 2, the water pipe 21 is divided outside the hollow piston 16 inside the bottom 14 of the sheath 12 or in front of it so as to feed the sprinkling nozzles placed in the bottom 14 of the sheath 12, there being ten of these nozzles in the embodiment shown here, namely three nozzles 27 for sprinkling of the receptacle R, six locking nozzles 28 and one nozzle 29 for sprinkling by the needle 5. The three sprinking nozzles 27 of the receptacle open into a recess 30 delimited by an internal face 31 of the wall of the bottom 14 and close to the bottom of this recess 30 not far from the opening 15, and are orientated (see also FIG. 4) sufficiently obliquely so as to project the water towards the bottom F of the receptacle R and with a sufficient lateral incidence so that, when the water rebounds onto the bottom F of the receptacle R towards the internal face 31, a vortex is produced on the entire surface of the internal face 31 which is thus completely sprayed and washed; the liquid droplets originally contaminating the needle 5 following any possible ill-timed projection flow through the opening 15 and then flow along the block 6 and then into a drain (not shown) situated below the tank bottom 2. This drain may be a simple gravity sprinkling collector and its conception does not require any particular refined additions as the filling chamber situated under the rotating plug 7 is able to remain polluted without constituting a drawback.

The internal face 31 is bent and smooth without any sudden change of slope which would produce nooks in which the droplets would tend to stagnate.

The six locking nozzles 28 fully open at the top of the recess 30 close to the height of the cylindrical portion 13 and emit low flow jets at low pressure, concurrent horizontal jets and tangent to the bottom F which complete washing this bottom F, especially as regards its cylindrical portion adjacent to its flat end face pricked by the needle 5. The purpose of the jets coming from the locking nozzles 28 is also to cut the original jet portions of the nozzles 27 for sprinkling the receptacle R which would rise up too far and could project droplets, possibly contaminated, onto the highest portions of the receptacle R. The locking nozzles 28 are situated above the nozzles 27 for sprinkling the receptacle R and their jets may also be laterally oblique so as to reinforce the vortex on the internal surface 31.

The nozzle 29 for sprinkling the needle is housed in the small ring 23 in the direction of the needle 5 and is used to clean the latter. It is a single nozzle but there could be several disposed around the needle 5. As this nozzle 29 is placed into operation after the other nozzles, when the water for washing the recess 30 and the bottom F has flowed out, this nozzle requires a special feeding network, which explains that one may be tempted to omit it from the device. Moreover, it is not absolutely essential and is rather a form of additional protection.

Figure 3:
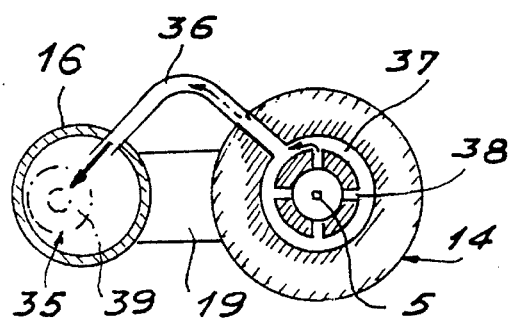
FIG. 3 is a section on the line III—III of FIG. 2.

The installation also includes a drying system, clearly visible on FIGS. 2 and 3, which includes a suction pump 35 at the bottom of the compressed air pipe 20 so as to locally create there a sectional contraction and partial depression; a pipe 36 opens at the neck of the suction pump 35 and ends in a throat 37 established behind the bottom of the internal face 31 and connected by only four orifices 38 to the recess 30. These orifices 38 are therefore suction orifices by which the water remaining from washing is sucked up from the internal face 31 and bottom F of the receptacle R and then ejected via the orifice 39 of the compressed air pipe 20. The suction device, by means of a combination of an air current and a static device for creating a partial depression, is advantageous as the air may be diverted from the air feeding of the transport pipes without really complicating the installation.

The receptacle R may be sent into the network 10 after drying. In order to do this, air is sent into the hollow piston 16 and into the air connection 19. The optical fiber 18 is able to ensure that a receptacle R is present at the bottom of the cage 24.

The boat 24 is pierced with a window 40 which normally reveals a portion of a small ring C of the receptacle R and situated immediately above the bottom F, the use of this small ring being to guide the receptacle R into the compressed air pipes and secondly to retain the receptacle R in the cage 24, thus preventing it from falling through the hole 26. The small ring C can be marked by the optical fiber 18 by virtue of its color or another identification characteristic.

Figure 4:
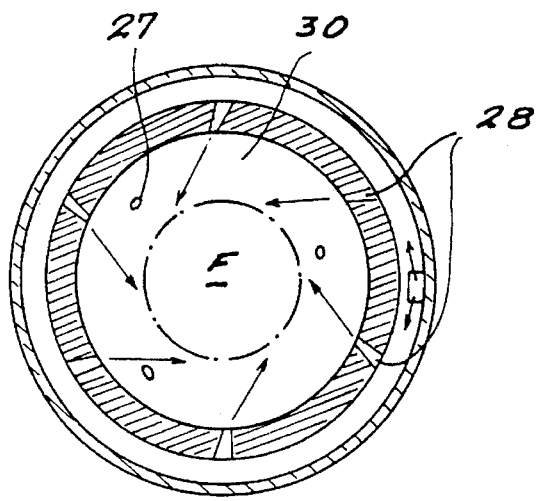
FIG. 4 is a detailed view of FIG. 3 illustrating the washing mode.

The washing shown on FIGS. 2 and 4 occurs when the sheath 12 and the cage 24 have been lifted up from the piercing needle 5 and come back to the position shown on FIG. 1 after the receptacle R has been filled.

Drying is effected after the sheath 12 has returned onto the block 6, the cage 24 remaining raised so as to space the bottom F from the needle 5 and block the opening 15 at the bottom of the recess 30 and enable the receptacle R to be sent towards the top and into the pneumatic transfer network by means of the air provided by the hollow piston 16.

What is claimed is:

1. Device for filling a receptacle comprising: a filling liquid elevator ended by a needle for piercing a bottom of the receptacle; a sheath having a bottom constituted by a wall comprising an opening in front of the needle and mobile towards the needle and being connected to a network of pipes equipped with pneumatic means for displacing the receptacle; and a cage situated in the sheath and disposed so as to suspend the receptacle slightly above the bottom of the sheath, wherein the sheath is equipped with nozzles for sprinkling washing liquid towards the bottom of the receptacle suspended in the cage and towards an internal face of the wall of the sheath, said internal face facing the receptacle and defining a recess at the bottom of the sheath, and some of the nozzles are oriented in such a way so as to sprinkle the internal face of the wall of the sheath obliquely and produce a vortex of the washing liquid in the recess.

2. Filling device according to caim 1, wherein some of the nozzles are orientated in such a way so as to sprinkle the bottom of the receptacle obliquely and produce a rebounding of the washing liquid from the bottom of the receptacle towards the internal face of the bottom of the sheath.

3. Filling device according to claim 2, wherein some of the nozzles are oriented towards the bottom of the receptacle, at a level of the bottom of the receptacle tangentially to an adjacent cylindrical portion of the receptacle.

4. Filling device according to claim 2, wherein the internal face is rounded without sudden change of slope.

5. Filling device according to claim 1, wherein the sheath is equipped with at least one nozzle for sprinkling liquid towards the needle.

6. Filling apparatus according to claim 1, wherein the sheath is equipped with means for drying the bottom of the receptacle and said internal face of the wall of the bottom of the sheath.

7. Filling device according to claim 6, wherein the drying means comprises means for sucking the washing liquid driven by a compressed air circuit provided with a static partial depression creation device.

8. Filling device according to claim 7, wherein the means for sucking comprises ports through the piercing.

9. Filling device according to claim 1, wherein the piercing communicates with the recess at a bottom of said recess.

10. Device for filling a receptacle comprising: a filling liquid elevator ended by a needle for piercing a bottom of the receptacle; a sheath having a bottom constituted by a wall comprising an opening in front of the needle and mobile towards the needle and being connected to a network of pipes equipped with pneumatic means for displacing the receptacle; and a cage situated in the sheath and disposed so as to suspend the receptacle slightly above the bottom of the sheath, wherein the sheath is equipped with nozzles for sprinkling washing liquid towards the bottom of the receptacle suspended in the cage and towards an internal face of the wall of the sheath, said internal face facing the receptacle and defining a recess at the bottom of the sheath, the sheath being equipped with means for drying the bottom of the receptacle and said internal face of the wall of the sheath, and the drying means comprising means for sucking the washing liquid driven by a compressed air circuit provided with a static partial depression creation device.

* * * * *